US012630791B2

(12) United States Patent
Pietras et al.

(10) Patent No.: US 12,630,791 B2
(45) Date of Patent: May 19, 2026

(54) BIOREACTOR SYSTEM FOR TISSUE ENGINEERING

(71) Applicant: OTTO-VON-GUERICKE UNIVERSITÄT MAGDEBURG, Magdeburg (DE)

(72) Inventors: Jan Patrick Pietras, Naumburg (DE); George Kensah, Göttingen (DE); Julia Dahlmann, Hannover (DE)

(73) Assignee: OTTO-VON-GUERICKE UNIVERSITÄT MAGDEBURG, Magdeburg (DE)

( * ) Notice: Subject to any disclaimer, the term of this patent is extended or adjusted under 35 U.S.C. 154(b) by 936 days.

(21) Appl. No.: 17/781,574

(22) PCT Filed: Dec. 2, 2020

(86) PCT No.: PCT/EP2020/084198
§ 371 (c)(1),
(2) Date: Jun. 1, 2022

(87) PCT Pub. No.: WO2021/110712
PCT Pub. Date: Jun. 10, 2021

(65) Prior Publication Data
US 2022/0411734 A1 Dec. 29, 2022

(30) Foreign Application Priority Data

Dec. 2, 2019 (EP) ..................................... 19213034

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/22* (2013.01); *C12M 23/26* (2013.01); *C12M 29/10* (2013.01);
(Continued)

(58) Field of Classification Search
None
See application file for complete search history.

(56) References Cited

U.S. PATENT DOCUMENTS 6,060,306 A 5/2000 Flatt et al.
7,682,822 B2 3/2010 Noll et al.
(Continued)

OTHER PUBLICATIONS

International Search Report and Written Opinion in corresponding PCT/EP2020/084198, dated Mar. 4, 2021.
(Continued)

*Primary Examiner* — William H. Beisner
(74) *Attorney, Agent, or Firm* — Hovey Williams LLP; Crissa A. Cook

(57) ABSTRACT

The present invention relates to a novel bioreactor system for preparing an engineered three-dimensional biological tissue construct. The bioreactor system comprises a cultivation chamber that is designed to allow the formation, cultivation and the subsequent testing and/or stimulation of tissue constructs on one or more support elements with a minimum risk of microbial contamination or mechanical damage. The invention furthermore relates to a method for preparing an engineered tissue construct using the novel bioreactor system. The invention also relates to the use of the bioreactor system for preparing engineered biological tissue constructs, preferably tissue constructs which are suitable for being used in clinical tissue replacement and reconstructive therapy, drug development, drug screening, toxicity testing, cosmetic studies, safety testing, developmental studies, disease modeling, or food purposes.

15 Claims, 3 Drawing Sheets

(51) Int. Cl.
    *C12M 1/12*          (2006.01)
    *C12M 1/42*          (2006.01)
    *C12N 5/071*        (2010.01)

(52) U.S. Cl.
    CPC ............ *C12M 35/04* (2013.01); *C12M 37/00*
            (2013.01); *C12N 5/0697* (2013.01)

(56)            References Cited

U.S. PATENT DOCUMENTS

| | | | |
|---|---|---|---|
| 10,233,415 B1 | 3/2019 | Mathur et al. | |
| 2008/0176318 A1* | 7/2008 | Wilson | C12M 23/24 |
| | | | 435/297.1 |
| 2010/0323438 A1* | 12/2010 | Porter | C12M 35/04 |
| | | | 435/293.1 |
| 2012/0199487 A1 | 8/2012 | Stelzle et al. | |
| 2016/0201037 A1 | 7/2016 | Tuan et al. | |
| 2017/0226462 A1* | 8/2017 | Wu | C12M 29/10 |
| 2022/0396753 A1* | 12/2022 | Pitoulis | C12M 35/04 |

OTHER PUBLICATIONS

Mathur, et al., "Human iPSC-based Cardiac Microphysiological System For Drug Screening Applications", Sci Reports, 2015, 5, 7 pages.
Pietras, et al., "Generation and Maturation of Human IPSC-Derived Myocardium in a Closed and Automated Bioreactor System", Thorac Cardiovasc Surg, 2021, 69(1), pp. S1-S85.

\* cited by examiner

BIOREACTOR SYSTEM FOR TISSUE ENGINEERING

RELATED APPLICATIONS

This application is the U.S. National Stage of International Patent Application No. PCT/EP2020/084198, filed Dec. 2, 2020, which is hereby incorporated by reference in its entirety, and which claims priority to European Patent Application No. 19213034.2, filed Dec. 2, 2019.

The present invention relates to a novel bioreactor system for preparing an engineered three-dimensional biological tissue construct. The bioreactor system comprises a cultivation chamber that is designed to allow the formation, cultivation and the subsequent testing and/or stimulation of tissue constructs on one or more support elements with a minimum risk of microbial contamination or mechanical damage. The invention furthermore relates to a method for preparing an engineered tissue construct using the novel bioreactor system. The invention also relates to the use of the bioreactor system for preparing engineered biological tissue constructs, preferably tissue constructs which are suitable for being used in clinical tissue replacement and reconstructive therapy, drug development, drug screening, toxicity testing, safety testing, developmental studies, disease modeling, or food purposes.

BACKGROUND OF THE INVENTION

The generation of solid three-dimensional tissue constructs is an emerging technology which will have drastic implications on many aspects of medicine and basic research. As three-dimensional tissue is superior to two-dimensional cell culture in mimicking the natural environment found in the living individual, it shows enhanced maturation of cells within the tissue and manifestation of a physiologic and mature phenotype.

Apart from providing a tissue source for reconstructive therapies in humans, three-dimensional tissue is particularly suitable for both ex vivo and in vivo studies, amongst others, human disease modelling, pharmacological drug development and screening, and drug safety testing. Compared to testing in animals or animal cell cultures or tissues, the reliability of results obtained from human tissue is higher due to the comparability of genetic background and physiological or pathophysiological responses to certain stimuli or resulting from genetic manipulations or mutations. For these reasons, the generation of human tissue constructs, enabled by the recently description of nuclear reprogramming resulting in induced pluripotent stem cells, has received considerable attention in the last decade.

So far, the preparation of three-dimensional tissues is associated with numerous challenges. In particular, the formation of tissue constructs is complex and requires labour-intense culture procedures making it prone to microbial contamination and mechanical trauma or damage.

Normally, three-dimensional tissue constructs are prepared by mixing a suspension of the intended cells, such as muscle cells, with a liquid matrix that is capable of forming a semi-solid hydrogel in a casting mold. After hardening, the tissue constructs are then removed from the molds and transferred to measuring or stimulation devices. Although efforts have been made in recent years to reduce as many manual steps as possible by automatization, tissue failure due to contamination or mechanical damage that occurs upon removal of the tissue constructs still is a serious problem of this technology. In particular, the removal of the tissue constructs from the molding form and the subsequent transfer of the constructs to other devices, e.g. for drug testing, is often associated with contamination and unintended tissue damage, e.g. by small fissures that impair their further use. Both issues have a considerable impact on the usability of the constructs and the reliability of the data generated by use of these constructs.

The present invention overcomes these problems by providing a closed and automatically perfused bioreactor system that allows for the generation and long-term cultivation of three-dimensional tissue in clinically relevant dimensions, as well as in miniaturized dimensions applicable to high throughput pharmacological, basic research and other applications. A particular advantage of the bioreactor system of the invention resides in the ability to form tissue construct on a support element, or preferably suspended between two support elements, without any manual intervention of the operator.

The bioreactor system of the present invention therefore allows for the reproducible preparation of tailored tissue constructs which are based on different cell types and can be maintained in the bioreactor system for subsequent measurements and tests as well as for stimulation of the tissue. In this way, contamination and mechanical damaging of the constructs is prevented.

DESCRIPTION OF THE INVENTION

Provided herein is a bioreactor system which allows for the preparation and subsequent testing of biological tissue constructs under defined conditions. Accordingly, in a first aspect, the present invention provides a bioreactor system for preparing an engineered tissue construct, said bioreactor system comprising at least the following items:
- (a) a cultivation chamber, said cultivation chamber comprising
  - a top plate, a bottom plate and at least one side wall which extends between to top plate and the bottom plate,
  - a first support element which is attached to one of the at least one side wall and extends into a cavity defined by the top plate, the bottom plate and at the least one side wall, wherein said first support element is adapted to enable formation of a tissue construct in contact therewith,
  - an inlet for introducing a fluid into the cavity said inlet being located between the top plate and the first support element,
  - an outlet for removing fluid from the cavity said outlet being located between the top plate and the inlet,
  - wherein the vertical distance between said first support element and the bottom plate is between 1-25 mm, and
- (b) optionally, at least one medium reservoir connected thereto.

The invention thus relates to a bioreactor system for preparing an engineered tissue construct, wherein the bioreactor system comprises a novel type of a cultivation chamber in which the preparation, cultivation and characterization of the tissue construct takes place. Within the bioreactor system of the invention, the cultivation chamber serves as a sterile vessel into which the cells and hydrogel components are introduced to form the tissue construct.

The cultivation chamber comprises a top plate, a bottom plate and at least one side wall, the latter of which extending between to top plate and the bottom plate. The cultivation chamber can have any shape, but it is particular preferred that the cultivation chamber is cubical in shape which means that the chamber comprises four side walls which form a closed cuboid with the top and bottom plate. The top plate, bottom plate and the one or more side walls can be made of the same or different materials. In one embodiment, at least the bottom plate consists of a biocompatible and chemically inert material. In a preferred embodiment, the bottom plate and the side walls of the chamber consist of a biocompatible and chemically inert material. In an even more preferred embodiment, the top plate, the bottom plate and the side walls consists of a biocompatible and chemically inert material. In a particularly preferred embodiment, the complete chamber consists of a biocompatible and chemically inert material.

For example, the one or more side walls of the cultivation chamber can comprise or consists of a flexible or semi-flexible material. As used herein, flexible materials refer to non-rigid materials that can be deformed. Similarly, semi-flexible materials refer to non-rigid materials that can be partially deformed. Suitable flexible materials comprise, for example, silicone. In a different design, the chamber can comprise or consists of different materials, e.g. a flexible or semi-flexible material and a rigid material. In this way, flexible material characteristics can be provided locally in predefined parts of the cultivation chamber as needed.

In another embodiment, the bottom plate of the cultivation chamber comprises, consists of or is coated with a material or compound that inhibits the adhesion of cells to the bottom plate. Since the tissue construct shall form on the one or more support elements, and preferably suspended between oppositely arranged elements, any adhesion of cells to the bottom plate, or the side walls is undesirable. Thus, in another embodiment, the bottom plate and the side walls of the chamber comprise, consist of or are coated with a material or compound that inhibits the adhesion of cells. For example, the bottom plate and the side walls can be coated with silanes or polymers, such as polyethylene glycol (PEG) or silicone.

In one embodiment, the top plate and/or the bottom plate of the cultivation chamber are transparent or semi-transparent so as to allow monitoring the development and/or responses to stimuli of the tissue constructs by microscopy, in particular live-view, bright-field and fluorescence-microscopy. In addition, transparent or semi-transparent top and bottom plates allow for the optical manipulation of excitable tissues or cells. This is particularly advantageous in opto-genetic approaches. For example, the constructs can comprise or consists of genetically modified cells, e.g. cells that harbor optogenetic protein expression systems that express or overexpress certain proteins which are able to respond to excitation by light, e.g. by opening ion channels. Such approaches can be useful for studying cell-to-cell communication within the biological construct as well as signaling pathways within cells. A transparent or semi-transparent top plate or bottom plate is also advantageous as it allows solidification or modification of extracellular matrix components, e.g. by multiphoton-mediated collagen cross-linking.

The chamber furthermore comprises a first support element which is attached to one of the at least one side walls and extends into a cavity defined by the top plate, the bottom plate and at the least one side wall. The first support element is adapted to enable formation of a tissue construct in contact therewith. It will be arranged in the cavity such that an engineered tissue construct can be formed in contact with said first support element.

While it is possible to provide only a single support element in the chamber, the use of more than one support element, such as two, three, four or more support elements, is clearly preferred. It is particularly preferred that the chamber comprises a first support element and a second support element. The second support element is preferably attached to the at least one side wall on an opposite side of the cavity with respect to the first support element and extends into the cavity such that an engineered tissue construct can form in contact with said first support element and said second support element. Accordingly, both support elements are preferably arranged at opposite side walls and extend into the cavity such that they provide a structure to which the consolidating tissue construct can attach. Preferably, the first and the second support elements have the same vertical distance to the bottom plate.

The first and the second support elements in the cultivation chamber are positioned with respect to each other such that the space between said first support element and said second support element preferably is between 1 and 150 mm, between 1 and 140 mm, between 1 and 130 mm, between 1 and 120 mm, between 1 and 110 mm, between 1 and 100 mm, between 1 and 90 mm, between 1 and 80 mm, between 1 and 70 mm, 1 and 60 mm, more preferably between 1 and 50 mm, between 1 and 40 mm, between 1 and 30 mm, between 1 and 20 mm, or between 1 and 10 mm. For example, the space between said first support element and said second support element can be between 5 and 150 mm, between 5 and 140 mm, between 5 and 130 mm, between 5 and 120 mm, between 5 and 110 mm, between 5 and 100 mm, between 5 and 90 mm, between 5 and 80 mm, between 5 and 70 mm, between 5 and 60 mm, 5 and 50 mm, between 5 and 25 mm, between 5 and 15 mm, or between 5 and 10 mm. In some embodiments, the space between said first support element and said second support element will preferably be between 10 and 150 mm, between 10 and 140 mm, between 10 and 130 mm, between 10 and 120 mm, between 10 and 110 mm, between 10 and 100 mm, between 10 and 90 mm, between 10 and 80 mm, between 10 and 70 mm, 10 and 60 mm, 10 and 50 mm, between 10 and 40 mm, between 10 and 30 mm, or between 10 and 20 mm. The length of the tissue construct that is formed between said first and said second support element will be determined by the space between those elements.

The one or more support elements, such as the first and the second support element, preferably comprise or consist of a biocompatible material. Suitable biocompatible materials are metallic materials including stainless steel, chromium and chromium alloys as well as titanium and titanium alloys. In a preferred embodiment, the one or more support elements comprise or consist of titanium or a titanium alloy. In another preferred embodiment, the one or more support elements comprise or consist of carbon or a carbon composite material.

The one or more support elements can have any shape which allows for the attachment of a biological tissue construct. In a simple embodiment, the one or more support elements have the form of a pin or stud. In a preferred embodiment, the one or more support elements may be formed as a triangle with one vertex of the triangle being attached to the side wall of the chamber. In yet another preferred embodiment, the one or more support elements are T-shaped or drumstick-shaped. Further, circular or rectangular shaped support elements may also be used in the cultivation chamber disclosed herein. In another preferred embodiment, the one or more support elements comprise a first elongated, rod-shaped portion and a second triangular-shaped portion. While the rod-shaped portion is attached to the side wall of the cultivations chamber, the triangular-shaped portion provides for the attachment of the tissue construct. In another preferred embodiment, the chamber comprises two support elements, and each of these support elements comprises a first elongated, rod-shaped portion and a second triangular-shaped portion connected thereto. The two triangular-shaped portions are aligned such that one side of the triangular-shaped portion of the first support element is aligned in parallel or essentially in parallel to a corresponding side of the triangular-shaped portion of the second support element. Such an arrangement of the support elements is depicted in FIGS. 2 and 3.

It has been found herein that by keeping the vertical distance between the one or more support elements and the bottom plate in the range between 1-25 mm, preferably 1-20 mm, more preferably 1-15 mm, and even more preferably 1-10 mm or 1-5 mm, the tissue constructs form onto or between the one or more support elements without any manual intervention. This means that by selecting the vertical distance between the one or more support elements and the bottom plate appropriately, it is no longer necessary to culture the tissue construct in a first device and subsequently transferring the construct for further analysis. Instead, it is possible with the novel device to form the tissue construct within the cultivation chamber onto or between the support elements which subsequently allow for a testing one or more of their characteristics without opening the chamber and exposing the constructs to an unsterile environment. In this way, the chamber of the invention constitutes a closed cultivation unit in which tissues can be prepared, cultivated, characterized, tested and stimulated in the same sterile environment without transfer to other devices. This is a particular advantage when preparing tissues for medical purposes. As used herein, the term vertical distance refers to the distance between the one or more support elements and the bottom plate along a straight line.

Preferably, the first support element is connected to a respective coupling element which allows the coupling of a sensor device, an electrical stimulation device, a measuring device and/or a force-generating device such as an electrical drive to the respective first support element. Even more preferably, each of the support elements of the cultivation chamber, for example the first and the second support element, is connected to a respective coupling element which allows the coupling of the support element with one or more additional devices, such as a sensor device, an electrical stimulation device, a measuring device and/or a force-generating device such as an electrical drive to the respective first and second support element. The function of the one or more coupling elements is to provide a sterile and load-carrying connection between the at least one support element and the additional device.

The one or more coupling elements can be magnetic or electromagnetic coupling elements. Alternatively, the connection can be realized through physical principles like low pressure or friction, e.g. press fitting or screwing, or chemical bonding. The coupling elements can be made of any material, but will be preferably made of a material with high strength and stiffness so that inaccuracies during measurements due to material properties are eliminated.

In one embodiment, the at least one support element is connected via a coupling element to a force sensor, an electrical sensor or a transducer. The force sensor, electrical sensor or transducer may record, preferably continuously, the active and passive forces that occur in the tissue construct during or after cultivation. The data may be collected and forwarded to a computational unit for further analysis. The force sensor, electrical sensor or transducer can be connected directly or indirectly to the coupling element.

In another embodiment, the at least one support element is connected via a coupling element to an electric or electromagnetic drive. It has been described in the literature that engineered tissue constructs, especially force-generating tissue constructs, such as contracting heart tissue, require a mechanical load (auxotonic, increasing isometric, or other) to be applied for optimum maturation. In order to apply such load, the coupling element can be connected to an electric or electromagnetic drive. This drive may generate a horizontal movement of at least one of the coupling elements and the one or more support elements connected thereto, thereby providing a mechanical load, either stretch or compression, to the tissue construct. The drive can be directly connected to the coupling element or indirectly via other elements which redirect the movement to become translational. For example, the one or more support elements can be directly connected to the side walls of a flexible or semi-flexible cultivation chamber and merely transfer a recurring deformation of the chamber which results, e.g. from a periodic change of the geometry of the cultivation chamber and hence applies mechanical load to the biological tissue. In one particularly preferred embodiment, the movement of one of the support elements is achieved by a connection to the coupling element, and the coupling itself is connected to a flexible part of the side wall that creates a translational movement due to a change of volume and/or geometry. In such embodiment, volume and/or geometry changes lead to the deformation of the flexible side wall which results in a translational movement of the coupling and support elements. In another embodiment, the translational movement of at least one of the support elements is achieved by an external electromagnetic or magnetic field. For example, the coupling element itself or an element associated thereto is made of a magnetic material that is attracted if the strength of the magnetic field is increased. By modulating the strength of the magnetic field, a support element in the chamber that is connected to the magnetic coupling element can be put into motion.

Where an electric or electromagnetic drive is connected to the one or more coupling elements, this drive preferably allows for a static, semi-static, or dynamic loading by applying isotonic, increasing isometric, auxotonic and/or isokinetic loads to the tissue construct. The coupling elements may include a flexible or semi-flexible element with a damping factor through which a pre-determined load can be applied to the tissue construct that is attached to the at least one support element.

The cultivation chamber of the present invention further comprises an inlet which is located between the top plate and the one or more support elements. The inlet is designed such that it allows the introduction of a fluid into the chamber while preferably preserving sterility inside the chamber. In a particular preferred embodiment, the chamber comprises more than one inlet, wherein each of said inlets is independently used for introducing a different fluid into the chamber. For example, the chamber can comprise a first inlet for introducing a cell-matrix suspension into the chamber, and a second inlet for introducing a suitable culturing medium. Depending on the composition of the matrix to be formed, the chamber can comprise 2, 3, 4, 5, 6 or more inlets. However, it is also possible to introduce the cell-matrix suspension and the culturing medium consecutively into the cultivation chamber by use of a single inlet.

The one or more inlets are located between the top plate and the support element. This means that the one or more inlets are positioned above the one or more support elements. This ensures that the fluid that is introduced through the one or more inlets can submerge the one or more support elements and the biological construct that is formed on or between the support elements. In some embodiments, the vertical distance between the one or more support elements and the one or more inlets is between 1-50 mm, between 1-40 mm, between 1-30 mm, between 1-20 mm, between 1-10 mm, or between 1-5 mm. In other embodiments, the vertical distance between the one or more support elements and the one or more inlets is between 5-25 mm, between 5-15 mm, or between 1-10 mm. The exact vertical distance between the one or more support elements and the one or more inlets will depend on the overall size of the cultivation chamber.

After the cell suspension and the matrix components have started to solidify on the at least one support element, or preferably between at least two support elements, the at least one inlet of the cultivation chamber will be used to perfuse the cultivation chamber with a suitable culturing medium. As used herein, a culturing medium or cultivation medium refers to a medium which is adapted to the growth requirements of the cells that are used for preparing the tissue constructs. A suitable culturing medium that can be used for perfusion is described in the below examples. However, it should be understood that any other culturing medium which has been described in connection with the preparation of engineered tissue constructs can be used as well.

In a preferred embodiment, the bioreactor system of the present invention comprises a cultivation chamber and at least one fluid reservoir or fluid container connected thereto. The cultivation chamber is preferably connected to the at least one fluid reservoir or fluid container via the inlet of the chamber. The fluid reservoir or fluid container can be, e.g. a culturing medium reservoir, a cell suspension reservoir and/or an excipient reservoir. Preferably, the bioreactor system of the present invention will comprise more than one, e.g. two, three, four or five fluid reservoir or fluid containers which are connected via tubes or pipes to the one or more inlets of the cultivation chamber. In one particularly preferred embodiment, the bioreactor system comprises a first fluid reservoir or fluid container which contains a suspension of the cells in admixture with the matrix components that are to be introduced into the cultivation chamber. This reservoir or container is kept at low temperature to prevent the mixture from solidifying outside the chamber, e.g. within the tubing that connects the reservoir or container with the inlet. A second fluid reservoir or fluid container comprises the culturing medium which is introduced into the chamber after the cell-matrix mixture starts to solidify. Alternatively, it is also possible that the bioreactor system comprises a first fluid reservoir or fluid container comprising a cell suspension and, separated therefrom, the components that make up the matrix, e.g. collagen and Matrigel, in a second fluid reservoir or fluid container. A third fluid reservoir or fluid container comprises the culturing medium which is introduced into the chamber after the cell-matrix mixture starts to solidify.

In some embodiments, additional reservoirs or containers can be provided, that comprise e.g. drug candidate substances for testing with the tissue constructs. Hence, in another preferred embodiment, the bioreactor system comprises additional fluid reservoirs or fluid containers, such as a fourth, fifth or sixth reservoir or container. Such embodiments are particularly useful, as the cells and hydrogel components normally have different optimum storage conditions that need to be observed. When using separate fluid reservoirs or fluid containers, the conditions inside these reservoirs or containers can be adapted to the specific component stored therein.

In one embodiment, the different reservoirs or containers are each connected to a separate tube which in turn flows backflow-free into a single master supply tube which is connected to the inlet of the cultivation chamber. This reduces the space requirements for connectors at the cultivation chamber and also lowers the risk for microbial contamination.

Each reservoir or container will typically be equipped with gas-permeable and liquid-impermeable ventilation means that prevents negative pressure and at the same time maintains sterile conditions inside the cultivation chamber. In one embodiment, the reservoirs or containers may comprise or consist of a flexible semi-flexible material that is capable of altering its volume with a decreasing liquid level. In those embodiments, the reservoirs or containers do not need additional ventilation means. In another embodiment, the reservoirs or containers can be designed as multi-part containers having an internal piston-like element and an outer cylinder-like casing which move relatively to each other when the liquid level inside the container decreases. In such embodiment, the introduction of liquids into the cultivation chamber can be regulated by means that control the pressure applied to the pistons of the reservoir or container.

The reservoirs or containers of the bioreactor system of the present invention can be made of different materials. Preferably, the reservoirs or containers will be made of a biocompatible, chemically inert material such as stainless steel, plastic or glass. The reservoirs or containers may be designed to effectively protect their contents from external influences like ultraviolet (UV) light and temperature changes. In a preferred embodiment, each of the different reservoirs or containers comprises heating and or cooling means that enable the operator to adjust certain temperature to each of the liquids which are to be introduced into the cultivation chamber. Alternatively, it is of course also possible to provide for a single reservoir or container which comprises several separated compartments for different fluids. The connections between the one or more reservoirs or containers of the bioreactor system and the cultivation chamber will allow for the introduction of the fluid into the cultivation chamber under sterile conditions. This will normally be achieved by sterile pipes or tubes which connect the different parts of the bioreactor and are well known in the field of bioreactor technology.

The cultivation chamber of the present invention further comprises an outlet which is located between the top plate and the inlet. The outlet is designed such that it allows the excess fluid to leave the cultivation chamber while preserving sterility in the chamber. The outlet is preferably located near the top plate which means that it can act as an overflow. If culturing medium is introduced into the cultivation chamber during perfusion, excess medium can leave the chamber via the outlet once a certain filling level is reached. In some embodiments, excess medium is removed from the chamber via the outlet by applying a negative pressure.

In a particular preferred embodiment, the chamber comprises more than one outlet, such as 2, 3, 4, 5, 6 or more outlets. By increasing the number of outlets, the volume of the culture medium which can be conducted through the cultivation chamber per unit time during perfusion can be increased. The one or more outlets are typically connected to one or more waste reservoirs or containers.

The waste reservoirs or containers can also be made of a biocompatible, chemically inert material, such as stainless steel, plastic or glass.

The connections between the one or more waste reservoirs or containers and the outlet of the cultivation chamber are typically provided in the form of sterile pipes or tubes which are commonly used for bioreactors in the field of fermentation technology. The function of the waste reservoirs or containers is to collect and store metabolized culture medium that is expelled from the cultivation chamber.

The metabolized culturing medium that is removed from the cultivation chamber can be analyzed for metabolic components or biomarkers that reflect the physiological state of the tissue construct, e.g. in terms of growth and differentiation. For this purpose, the pipes and tubes that are connected to the one or more outlets of the cultivation chamber and/or the waste reservoirs or containers can comprise sensors for measuring the pH and/or the concentration $CO_2$ and $O_2$ in the metabolized medium. The measured information can be processed and stored by a computational unit that automatically adjusts the supply with fresh medium when needed. Alternatively or in addition, the metabolized medium can be analyzed by routine chemical or biochemical analyses, such as chromatography, electrophoresis and others.

In one embodiment, the at least one waste reservoir or container comprises gas-permeable and liquid-impermeable ventilation means for degassing and establishing pressure balance. In one embodiment, the at least one waste reservoir or container can comprise or consist of flexible or semi-flexible material which adjusts its volume to the inflowing liquid waste so that degassing becomes superfluous. In another embodiment the at least one waste reservoir or container is temperature-controlled so that the collected fluid can be preserved for further analysis without modification on a chemical or biological level. The at least one waste reservoir or container can also be equipped with a valve which allows withdrawing samples under sterile conditions. The filling level of the at least one waste reservoir or container is preferably monitored continuously to prevent overflowing or signal leakage.

The cultivation chamber itself may also comprise one or more gas-permeable and liquid-impermeable ventilation means for degassing. Further, the cultivation chamber has an inner geometry that provides for an optimized flow of fluids which are introduced into and released out of the chamber. In particular, it allows the culture medium introduced during perfusion to flow around the tissue construct such that a sufficient amount of nutrients are delivered to the cells of the tissue construct and metabolized compounds are removed. At the same time, the flow should be such that the shear stress exerted on the outer cell layers of the tissue construct is minimized or controlled to reduce or control stress reactions that might disturb or impair growth and maturation of the tissue construct.

According to the invention, the exact size of the cultivation chamber is not limited and will be adapted dependent on the desired size of the tissue constructs. A preferred size (length×width×height) of a cultivation chamber for preparing small construct will be about between 7×5×5 mm and 15×10×10 mm. Another preferred size (length×width× height) of a cultivation chamber for preparing small constructs will be about between 7×7×5 mm and 15×15×10 mm. A preferred size (length×width×height) of a cultivation chamber for preparing large construct will be about between 70×50×50 mm and 150×100×100 mm. Another preferred size (length×width×height) of a cultivation chamber for preparing large constructs will be about between 70×70×50 mm and 150×150×100 mm.

The cultivation chamber will typically comprise means for measuring and adapting the temperature inside the chamber. In particular, the chamber will typically be equipped with a heating device which allows providing for an optimum temperature that promotes growth of the cells cultured within the chamber. If the chamber itself does not comprise a heating device, it can be used in an incubator to provide the desired temperature. In addition, the cultivation chamber may further be equipped with probes for measuring the conditions inside the chamber, e.g. temperature, $O_2$, $CO_2$, and the like. The chamber can also comprise one or more inlets for introducing $O_2$ or $CO_2$ in order to adapt the conditions to the growth requirement of the cells. In one embodiment, the chamber comprises at least one inlet for introducing $O_2$ into the chamber. In another embodiment, the chamber comprises at least one inlet for introducing $CO_2$ into the chamber.

Apart from the cultivation chamber and the reservoirs or containers connected to the chamber, the bioreactor system of the present invention may comprise further components, such as a sterilization unit. In one embodiment, the pipes or tubes which are connected to the one or more inlets and provide for the introduction of the cell and hydrogel matrix components are equipped with one or more sterilization units. In this way, it is ensured that the components running through the pipes and tubes remain sterile upon entry into the cultivation chamber. Typically, the pipes and tubes will be sterilized before use. To further improve sterility of the bioreactor system, the connection between the tubes and the cultivation chamber can be subjected to a temporally controlled UV light source, preferably UV light having a wavelength of between 200 and 300 nm, or other means such as sterilization filters. Alternatively, sterility of certain components of the bioreactor system can be achieved by temperature shifts or plasma exposure prior to use.

The bioreactor system of the present invention may also comprise a light source. The light source will preferably be located above the top plate and allows for monitoring the tissue constructs by light-microscopy. In another embodiment a light source is located beneath the cultivation chamber to allow for fluorescence microscopy. In one embodiment, the light source generates high-energy light of a wavelength, which can be used for monitoring, controlling or pacing optogenetically modified cells or tissues, or to manipulate extracellular matrix components e.g. by multiphoton-mediated collagen cross-linking.

The bioreactor system of the present invention may also comprise a device for pacing the biological tissue in the cultivation chamber. A pacing device can be any device that transfers a current to the biological tissue in the cultivation chamber.

Also included herein is a bioreactor system that comprises more than one cultivation chamber. In a preferred embodiment, the bioreactor system comprises at least a first and a second cultivation chamber which are connected with each other such that the outlet of the first cultivation chamber is connected to the inlet of the second cultivation chamber. Culturing medium that is introduced into the first cultivation chamber can be transferred to the second cultivation chamber being led into the waste reservoir. In a preferred embodiment, more than two cultivation chambers are connected in this way, e.g. 3, 4, 5, 6, or more cultivation chambers, to mimic physiological interactions between different organs in vivo. In an even more preferred embodiment, the cultivation chambers are connected, either in parallel or in line, such that cultivation chambers that harbour medium-modifying tissue constructs are connected to cultivation chambers that enclose medium-consuming tissue constructs so as to simulate the physiological interactions that take place between organs in a living individual.

In another aspect, the invention relates to a method for preparing an engineered tissue construct, said method comprising:

providing a bioreactor system as described herein above,
    introducing cells and matrix components into the cavity of the cultivation chamber such that said first support element or both said first and second support elements is/are completely submerged in the fluid containing said cells and matrix components;
    incubating the cells and matrix components in the cultivation chamber under conditions that allow the formation of a tissue construct in contact with said first support element or both said first and second support elements of the reaction chamber.

The above method aims at the preparation of an engineered tissue construct, preferably a human engineered tissue construct, using the above-described bioreactor system. The tissue construct is formed from cells and hydrogel matrix components in accordance with commonly known protocols. Typically, a suspension of cells is mixed with one or more fluids that comprise hydrogel matrix components. The cell-matrix mixture solidifies to form a solid cell-containing matrix. Hardening of the matrix is typically dependent on the concentration of the matrix components and external conditions, in particular temperature and pH or concentration of crosslinking enzymes or substances. Accordingly, it is possible to modulate the time until hardening by selecting the temperature, pH and the concentrations of the matrix components in the cultivation chamber.

In a first step of the method, a bioreactor system as described above is provided. In a subsequent step, the required cells and matrix components are introduced into the cultivation chamber of the bioreactor system. Preferably, the cells and matrix components are pre-mixed and subsequently introduced as a mixture into the cultivation chamber. As described above, it is however also possible to introduce cells and matrix components consecutively, i.e. in the form of separate fluids, that are mixed in the cultivation chamber.

The fluids containing the cells and matrix components are introduced such that said first support element, and where applicable all support elements, are completely submerged in the fluid. In a preferred embodiment, the fluid containing the cells and matrix components is introduced such that the fluid level is between 5-50 mm, between 5-25 mm, and more preferably between 5-10 mm above the at least one support element. In a most preferred embodiment, the fluid containing the cells and matrix components is introduced such that the vertical distance between the top surface of the liquid level and the at least one support element is essentially the same as the vertical distance between the bottom plate and the at least one support element. In such an embodiment, the support element is arranged such that the liquid column above the at least one support element is identical to the liquid column beneath said element.

In the next step of the claimed method, the cells and matrix components are incubated in the cultivation chamber under conditions that allow the formation of a tissue construct in contact with said first support element of the reaction chamber. This means that the cells and matrix components are incubated at a suitable temperature and under appropriate conditions of $O_2$ and $CO_2$.

It is also possible to repetitively introduce cell-matrix components into the cultivation chamber to form a three-dimensional tissue construct that comprise different layers of cells and matrices. For this purpose, cell-matrix components are introduced into the cultivation chamber and incubated until the matrix solidifies. Then, further cell-matrix components are led into the cultivation chamber so that another layer is formed on the first solidified tissue layer. In this way, composite tissues can be formed.

Preferably, the method is performed with a cultivation chamber having at least two support elements, such as two, three or four support elements. Where two or more support elements are used, the tissue construct that forms by consolidation of the cell-matrix mixture will become suspended between the support elements. Once the matrix solidifies, it is preferred to perfuse the cultivation chamber with a suitable culturing medium. Thus, in a preferred embodiment of the method, the incubation step of the method comprises the perfusion of the cultivation chamber with culturing medium.

In one embodiment, the tissue construct prepared according to the method of the invention is particularly suitable for being used for medical purposes, such as for clinical tissue replacement and reconstruction therapy, drug development, drug screening, toxicity testing, safety testing, cosmetic studies, developmental studies, or disease modeling. In another embodiment, the tissue construct prepared according to the method of the invention is particularly suitable for being used for the preparation of food items, such as artificial meat. In light of a growing world population and an increasing demand for meat, the invention represents a valuable contribution for producing in vitro meat from stem cells of swine, cow, sheep or other species on an industrial scale. In another embodiment, the tissue construct prepared according to the method of the invention is skin tissue that is used for cosmetic studies, e.g. to determine the compatibility of cosmetic agents which are intended for administration to skin.

In yet another aspect, the invention relates to the use of the bioreactor system as described above for preparing an engineered tissue construct, preferably a human tissue construct that is suitable for being used in tissue replacement therapy, drug development, drug screening, toxicity testing, safety testing, cosmetic studies, developmental studies, disease modeling, or food purposes.

BRIEF DESCRIPTION OF THE FIGURES

In the following, an embodiment of the invention will be explained in more detail with reference to the drawings, in which.

Figure 1:
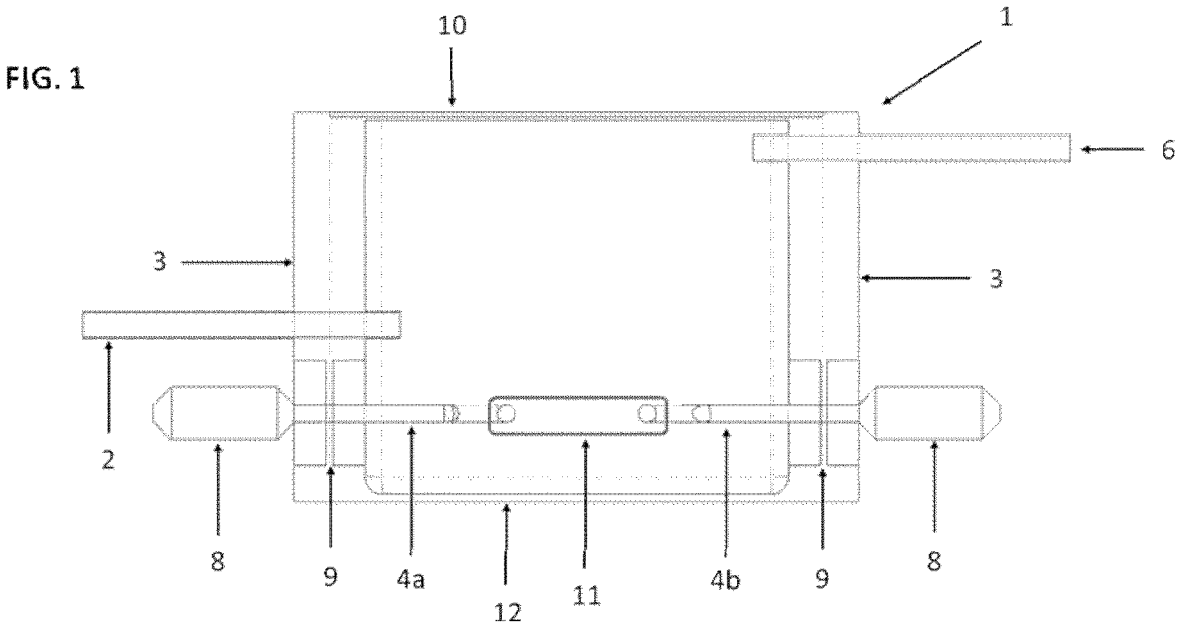
FIG. 1 is a cross-sectional view of the cultivation chamber of a bioreactor system according to a particularly preferred embodiment of the invention.

The cultivation chamber 1 shown in FIG. 1 is a small closed container that has a rectangular base area. The cultivation chamber 1 comprises a transparent top plate 10 and a transparent bottom plate 12 to allow monitoring tissue development within the chamber. The cultivation chamber 1 further comprises side walls 3 which define the spatial boundary. The cultivation chamber 1 comprises a first support element 4a and a second support element 4b which are attached to and extend from opposite side walls 3 into the cultivation chamber 1. The first support element 4a and the second support element 4b are located at the same vertical distance from the bottom plate which means that they extend into the lumen of the cultivation chamber 1 in the same horizontal plane. This is particularly advantageous as it facilitates the formation of the tissue construct 11 which is attached to the first support element 4a and the second support element 4b. The cultivation chamber 1 comprises an inlet 2 which provides a connection for a tube that can be used for introducing a cell-matrix suspension and culture medium into the lumen of the cultivation chamber 1.

If a tissue construct is to be prepared in a cultivation chamber having only a single inlet, as shown in FIG. 1, all components of the mixture that forms the final tissue construct are introduced through inlet 2 into the lumen of the cultivation chamber 1. It is advantageous that the inlet 2 is connected to a branched tubing system. In this way, the feeding of liquids from different reservoirs or containers into the chamber becomes feasible, and the liquid components that make up the tissue construct can be stored separately from each other without any contact of the components outside the cultivation chamber 1.

The inlet 2 is located above of the first support element 4a and the second support element 4b which means that the vertical space between the inlet 2 and the bottom plate 12 is greater than the vertical space between the support elements and the bottom plate 12. This allows the introduction of fluid through the inlet 2 such that the support elements are completely submerged. Only if the support elements 4a and 4b are completely submerged so that an autonomous attachment of the solidifying tissue construct 11 between the support elements 4a and 4b can be achieved. Typically, a suspension containing the cells which form the basis of the tissue constructs, e.g. muscle cells, is mixed with matrix components outside the cultivation chamber in a cooled reservoir or container at 4° C. and the mixture is then introduced into the cultivation chamber 1. The cells may be suspended in a buffer or in a suitable culture medium. When all components of the reconstitution mixture have been introduced into the chamber, the chamber is heated to a temperature of 37° C. to allow for the solidification of the reconstitution mixture.

When the tissue starts to solidify, the cultivation chamber 1 is completely filled with a suitable culture medium through inlet 2 to maintain viability of the cells. The medium is introduced with a defined flow rate which is selected dependent on the size and volume of the cultivation chamber 1. By maintaining a continuous flow into the chamber, it is assured that the cells that form the tissue construct are perfused with medium during the incubation step. The chamber further comprises an outlet 6 which is located near the top plate. Excess medium can leave the cultivation chamber through outlet 6. The outlet 6 is connected to a waste reservoir or container via suitable pipes or tubing. The tissue construct 11 that is formed attaches to the support elements 4a and 4b and becomes suspended between those elements without manual intervention. This is particular advantageous since the risk of contamination or mechanical damage is minimized.

In the embodiment depicted in FIG. 1, each of the support elements 4a and 4b is connected to a coupling element 8, the latter of which can be used for connecting further devices, such as in electric drive or a measuring device. To maintain sterility within the cultivation chamber 1, coupling elements 8 are connected with support elements 4a and 4b by a sterile membrane 9.

Figure 2:
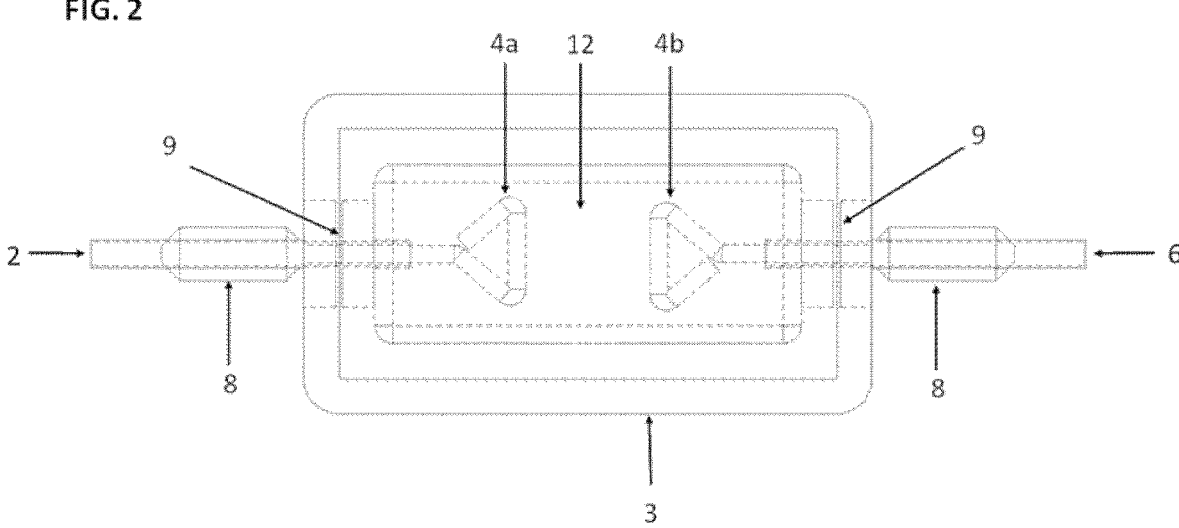
FIG. 2 is a top view of the cultivation chamber of a bioreactor system according to a particularly preferred embodiment of the invention.

FIG. 2 shows the top view of the cultivation chamber depicted in FIG. 1. It is depicted in dashed lines that the support elements 4a and 4b each comprise an elongated portion which extends into the lumen of the chamber and is connected to a triangular bracket that provides a sufficiently high surface area for providing a connection to the tissue construct 11. The triangular portions of the support elements 4a and 4b are arranged such that one side of each triangular bracket is aligned in parallel to the respective side of the adjacent bracket. In the depicted embodiment, the chamber is designed for the preparation of small constructs and hence the parts of the bracket aligned in parallel are each 3 mm in width, and the distance between the brackets is 3-5 mm.

Figure 3:
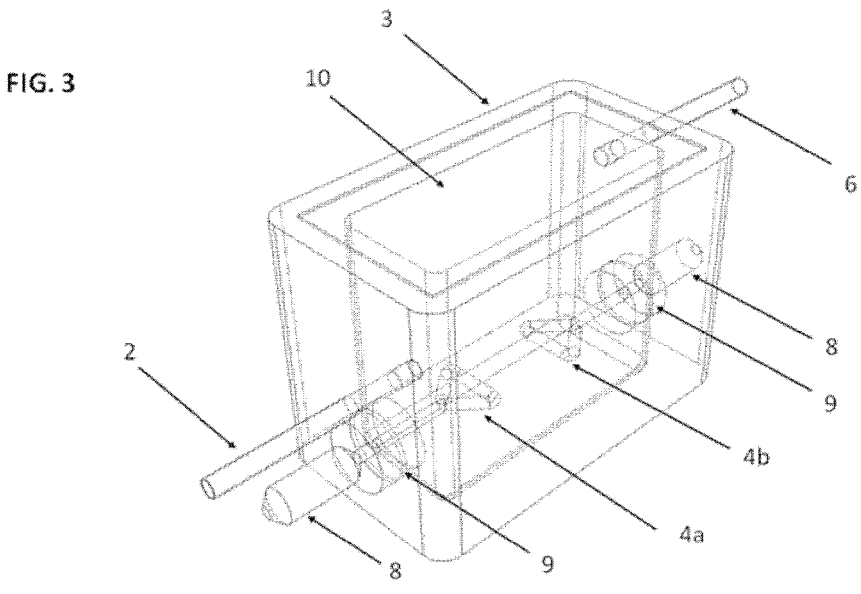
FIG. 3 is a perspective view of the cultivation chamber of a bioreactor system according to a particularly preferred embodiment of the invention.

FIG. 3 shows another perspective of the cultivation chamber 1 of the bioreactor system according to the invention. It can be seen that the inlet 2 is located above the coupling element 8 that is connected to the support element 4a and the outlet 6 is located above the inlet 2, immediately beneath the top plate 10.

Figure 4:
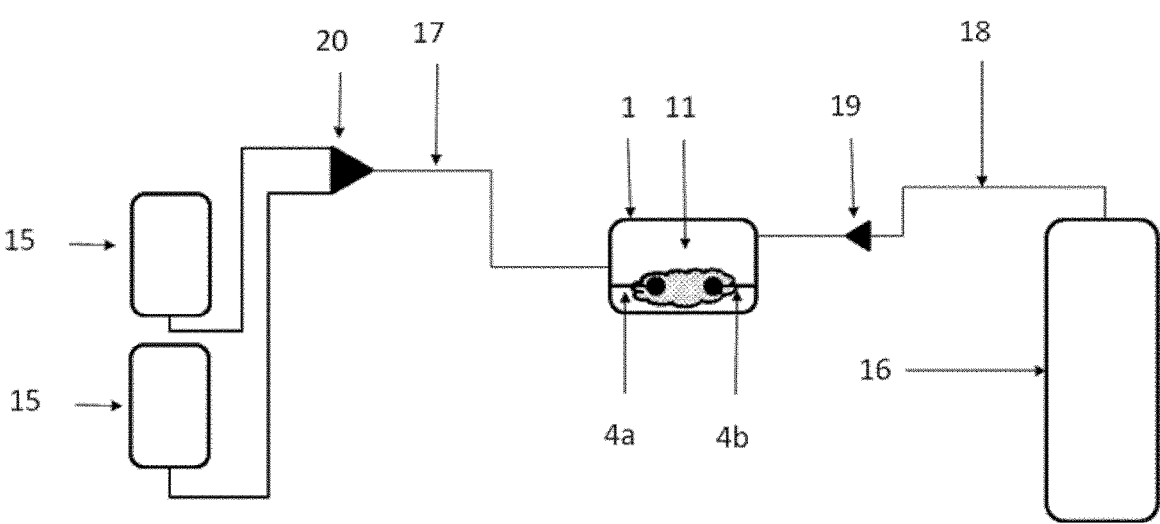
FIG. 4 is a schematic depiction of a bioreactor system according to a particularly preferred embodiment of the invention.

FIG. 4 shows a schematic depiction of bioreactor system according to the invention. The cultivation chamber 1 comprises a first support element 4a and a second support element 4b which are spaced from each other to allow a tissue construct 11 to become suspended between them. In addition to the cultivation chamber 1, the bioreactor system comprises supply tubes 17 for introducing the cell-matrix suspension and the culture medium into the cultivation chamber 1. In FIG. 4, the bioreactor system comprises two reservoirs 15 for storing the components for preparing the tissue construct, e.g. a reservoir for the cell-matrix suspension and a reservoir for culturing medium. The fluids are transported via valve 20 through supply tubes 17 into the cultivation chamber 1. Once the tissue construct has formed between the first support element 4a and the second support element 4b, the cultivation chamber 1 is completely filled and perfused with culture medium. Excess medium leaves the cultivation chamber 1 via drain tubes 18. The drain tubes 18 are equipped with a back-pressure valve 19 to prevent the backflow of used medium into the chamber. The medium is transferred into the waste reservoir 16 and can be discarded or further analyzed.

Figure 5:
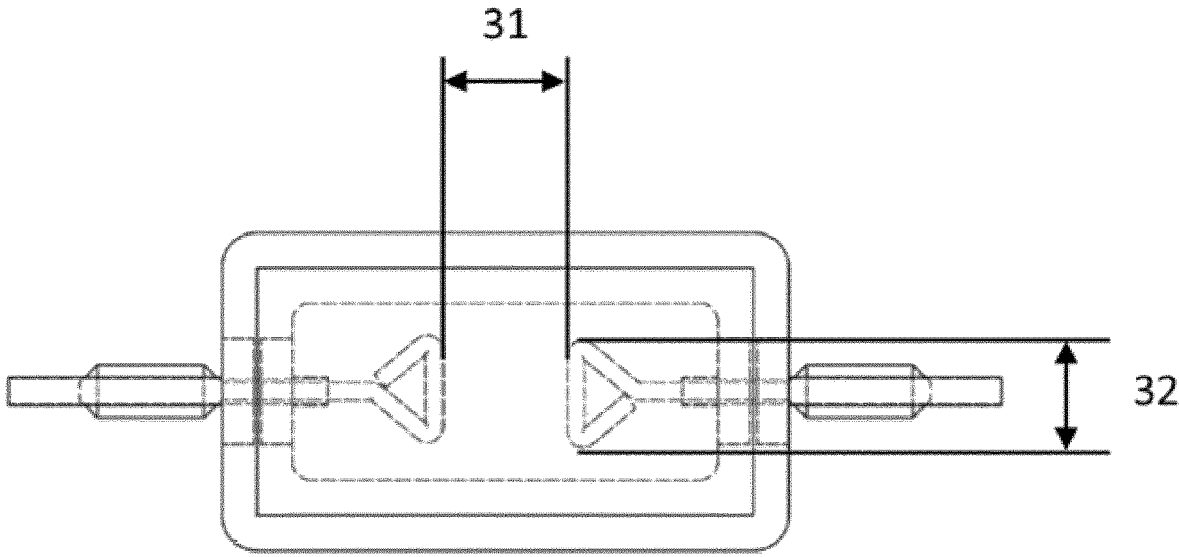
FIG. 5 shows a top view of the cultivation chamber of a bioreactor system according to a particularly preferred embodiment of the invention and the dimensions of the support elements as well as their distance with respect to each other.

FIG. 5 shows the a top view of the cultivation chamber depicted in FIG. 1 and in particular the dimensions of the first support element 4a and the second support element 4b and their distance with respect to each other. In this case, the parallel sides of the triangular brackets of the first support element 4a and the second support element 4b are spaced from each other by distance 31 which in this embodiment is 50-60 mm, depending on the size of the tissue construct to be synthesized. In the case of small tissue constructs, distance 31 will be preferably be 3-5 mm, while in the case of large tissue constructs, distance 31 will be preferably be 40-50 mm. Further, the sides of the triangular brackets of the first support element 4a and the second support element 4b have a width 32 which is in the range of 3-5 mm for small tissue constructs, and 30-45 mm for large tissue constructs.

EXAMPLES

The following examples are provided in order to illustrate the invention. It should however be understood that the scope of the invention is not limited by the examples. A skilled person will understand that several modifications can be made without deviating from the scope of the invention.

Example 1

Preparation of Large Human Fibroblast Biological Constructs

Fibroblast tissue constructs were prepared using liquid rat tail collagen type I (5 mg/mL, Cultrex, USA) and Matrigel (11 mg/mL, BD, USA) together with single cell suspensions. For the preparation of large tissue constructs, a cultivation chamber as described herein above having a size of 55 mm×55 mm×25 mm was used. The following volumes (final amounts per tissue construct in brackets) were mixed together on ice: 4.856 mL rat tail collagen type I (24.26 mg), 13.125 mL 2×PBS, 0.525 mL 0.4 M NaOH to neutralize the acidic collagen suspension and 2.624 mL Matrigel (28.88 mg). This matrix mixture was then mixed $5 \times 10^7$ human foreskin fibroblasts (HFF-1, American Type Cell Collection, USA) and suspended in 15.050 mL of the cultivation medium set forth in Table 1.

TABLE 1

| Cultivation medium | |
|---|---|
| Compound | Volumes/Concentrations |
| DMEM (4.5 g/mL glucose) | 346 mL |
| Horse serum | 42 mL |
| Human recombinant Insulin (10 mg/mL) | 400 μL |
| L-Glutamine (200 mM) | 4 mL |
| Ascorbic acid 2-phosphate (30 mM) | 400 mL |
| Penicillin Streptomycin (100 U/mL, 100 μg/mL) | 4 mL |
| Sum | 400 mL |

A cell-matrix mixture with a total volume of 36 mL was injected into the cultivation chamber via a 50 mL syringe, which was connected with one inlet of the cultivation chamber via a Luer lock. Subsequently, the inflow and outflow tubes were connected to the respective sites at the cultivation chamber, which was then placed in an incubator at 37° C. The medium reservoir, consisting of two 50 mL syringes placed in a syringe pump (B. Braun, Germany), was located outside of the incubator. The tube for introducing the culture medium into the cultivation chamber was pre-warmed by guiding the tubes through a water bath (37° C.) before reaching the cultivation chamber. The tube connected to the outlet was guided into a waste container. After a solidification period of 45 minutes, the cultivation chamber was completely filled with 40 mL of pre-warmed cultivation medium and subsequently perfused with 40 mL per day for the following seven days. Empty medium reservoir syringes were changed under sterile conditions if necessary. In total, 320 mL cultivation medium was used over the whole cultivation period. Microscopic assessment of the tissue constructs during cultivation was done using an inverted microscope (Evos XL Core, Thermo, USA). The transparent bottom plate of the cultivation chamber allowed for constant optical assessment of tissue morphology and maturation.
Results:

After injection into the square-shaped cultivation chamber, human foreskin fibroblast tissue constructs consolidated within the first 24 hours of cultivation. After seven days of automated perfusion the tissue constructs were removed for further analysis. The solid three-dimensional tissue construct was suspended between the support elements and revealed a high robustness against repeated folding and unfolding, indicating a high level of resilience to external mechanical stress.

Example 2

Preparation of Small Human Fibroblast Constructs

Figure 6:
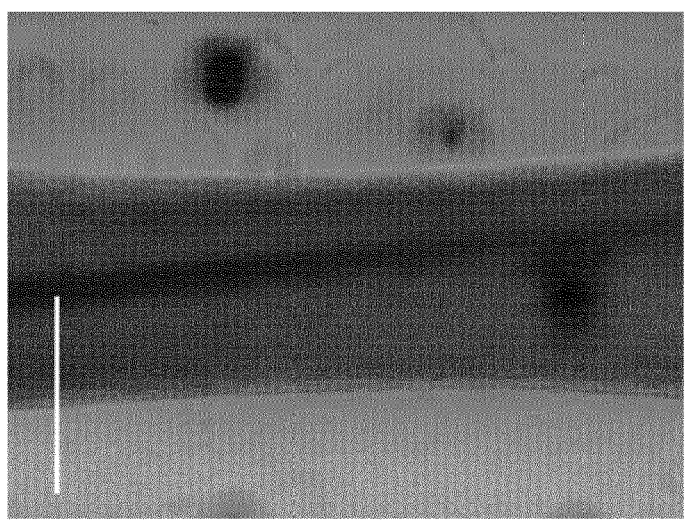
FIG. 6 shows the tissue construct made of $5 \times 10^5$ human foreskin fibroblasts. After 14 days of culturing, the initial cell and matrix mixture consolidated to form a solid, rod-shaped tissue construct. The scale bar shown corresponds to 500 μm.

To test whether the automated culture approach described in Example 1 was also feasible in a miniaturized fashion, smaller culture vessels were used in combination with a reduced number of cells. Three fibroblast tissue constructs were prepared in vessels having a size of 5 mm×12 mm×10 mm. The following compounds were mixed in the recites volumes on ice (final amounts for each tissue construct in brackets): 200 μL collagen type I (328.57 μg), 300 μL 2×PBS with $Ca^{2+}$ and $Mg^{2+}$, 30 μL 0.4 mM NaOH to neutralize the acidic collagen suspension and 100 μL Matrigel (373.3 μg). The matrix mixture was mixed with $1.5 \times 10^6$ HFF cells suspended in 430 μL of cultivation medium, resulting in $5 \times 10^5$ HFF cells per tissue construct. After injection into the cultivation chamber, the chamber was placed in an incubator under conditions described in Example 1 above. After a consolidation period of 45 minutes, each chamber was filled up with 341.3 μL pre-warmed medium and subsequently perfused with cultivation medium constantly for the cultivation period (2.5 mL per day). Empty medium reservoir syringes were changed under sterile conditions when necessary. For fibroblast tissue constructs, a 14 day cultivation time required 35 mL cultivation medium.
Results:

After injection into the cultivation chamber, the small fibroblast tissue constructs consolidated within the first 24 hours of cultivation. Over the course of a cultivation period of 14 days, a solid rod-shaped fibroblast tissue construct was observed which was suspended between the support elements of the cultivation chamber (FIG. 6). This demonstrates that the automated approach is cleanly amenable to different sizes.

Example 3

Preparation of Small Human Myocardium Constructs

To show that also metabolically highly active tissue constructs can be prepared by the bioreactor system of the invention, miniaturized tissues made of $10^6$ human iPSC-derived cardiomyocytes and $10^5$ fibroblasts were generated using the small cultivation system approach with an adjusted medium perfusion of 5 mL per day. For the preparation of cardiomyocyte-based tissue constructs, multiple incubation chambers having a size of 5 mm×12 mm×10 mm as described in Example 2 were used. The following compounds were mixed in the recites volumes on ice (final amounts for each tissue construct in brackets): 200 collagen type I (328.57 μg), 300 μL 2×PBS with $Ca^{2+}$ and $Mg^{2+}$, 30 μL 0.4 mM NaOH to neutralize the acidic collagen suspension and 100 μL Matrigel (373.3 μg). The matrix was mixed with $3 \times 10^6$ iPSC-derived cardiomyocytes (>98% purity) together with $3 \times 10^5$ HFF cells suspended in 430 μL cultivation medium resulting in $10^6$ iPSC-derived cardiomyocytes and $10^5$ HFFs per tissue construct. Of the 1.06 mL cell-matrix mixture, 353.33 μL were injected into one cultivation chamber via a 1 mL syringe attached to the inlet via a Luer lock. After a consolidation period of 45 minutes, each chamber was filled up with 341.3 μL pre-warmed medium and subsequently perfused with cultivation medium constantly for the cultivation period (5 mL per day). Empty medium reservoir syringes were changed under sterile conditions when necessary. Within 14 days, a total volume of 70.5 mL of cultivation medium was used per cardiomyocyte tissue construct. A cultivation period of 21 days required a total of 105.5 mL per cardiomyocyte tissue construct.

The tissue constructs were subjected to physiological measurements. Spontaneous, as well as electrically paced (±20 V, 5 ms) contraction forces were recorded with a measuring range of 0-100 mN (LSB 200, FUTEK, USA). During measurements, tissue constructs were stretched by 200 μm increments up to 1.6 mm preload using a linear drive (LM1247-020, Faulhaber, Germany) to detect a physiological force to preload relation, to determine the maximum contraction force and the changes of diastolic forces in response to increased preload.

Results:

In line with state-of-the-art approaches, solid three-dimensional tissue formed within the first 24 hours of tissue culture, with spontaneous contractions microscopically visible starting from day two to four. Increases in spontaneous contraction and diastolic forces of tissue constructs in response to the increasing preload of a single tissue were noted for days 14 and 21, respectively. This reflects the physiological response of cardiac tissue to an increasing preload, i.e. the Frank-Starling mechanism. Further physiological properties of the cardiomyocyte tissue constructs such as maturation, were indicated by a decrease of spontaneous beating frequency and an increase of contractile forces over cultivation time. Contractile tensions above 5 $mN/mm^2$ were observed after 21 days of tissue culture.

These results are comparable with data from state-of-the-art approaches using a similar consolidating hydrogel cell mix-approach under conventional cultivation in an open system. This confirms competitiveness of the presented system in terms of biocompatibility in combination with the advantages of being a closed and largely automated cultivation approach.

Example 4

Histologic Analysis

For histologic examination, the tissues prepared in the preceding examples were embedded in TissueTek (Sakura, Japan), snap frozen in liquid nitrogen and cryosections of 7 μm thickness were prepared using a HM 500 cryostat (Microm, Germany). Sections were fixed with paraformaldehyde (4%) and subjected to either conventional H&E staining or to immunofluorescence staining. The tissue constructs were examined for different extracellular and functional proteins, including collagen type I, vimentin, sarcomeric alpha-actinin, and connexin 43 by fluorescence microscopy using an inverted fluorescence microscope (Evos FL auto, Thermo, USA).

Results:

Histological examination of the fibroblast tissue constructs revealed an even distribution of cells and collagen throughout a cross-section of the tissue construct. Furthermore, the initial sphere-like appearance of fibroblast within the tissue on day 3 turned into a more mature phenotype, being elongated and highly interconnected. The tissue constructs consisted of viable cells throughout the tissue and vimentin-expressing fibroblasts in parallel orientation.

Histological examination of the cardiomyocyte tissue constructs on cultivation days 14 and 21 revealed an even distribution of cells throughout the tissue and iPSC-derived cardiomyocytes organized in parallel and in line with the axis of contraction showing well-developed sarcomeres. The gap junction protein Cx43 was more prominent in iPSC-derived cardiomyocytes on day 21, suggesting that maturation has taken place over time.

The invention claimed is:

1. A bioreactor system for preparing an engineered tissue construct, said system comprising:
   a cultivation chamber (1) comprising
      a top plate (10), a bottom plate (12) and at least one side wall (3) extending between the top plate (10) and the bottom plate (12),
      a first support element (4a) which is attached to the at least one side wall and extends into a cavity defined by the top plate (10), the bottom plate (12) and the at least one side wall (3), wherein said first support element (4a) is adapted to enable the formation of a tissue construct in contact therewith,
      a second support element (4b) which is attached to the at least one side wall on an opposite side of the cavity with respect to the first support element and extends into the cavity such that an engineered tissue construct can form in contact with said first support element (4a) and said second support element (4b),
      an inlet (2) for introducing a fluid into the cavity which is located between the top plate (10) and said first support element (4a),
      an outlet (6) for removing fluid from the cavity which is located between the top plate (10) and the inlet (2),
   wherein the vertical distance between said first support element (4a) and the bottom plate (12) is between 1-25 mm.

2. The bioreactor system of claim 1, wherein said top plate (10) and said bottom plate (12) of the cultivation chamber are transparent or semi-transparent.

3. The bioreactor system of claim 1, wherein said inlet (2) of the cultivation chamber is connected to a culturing medium reservoir, a cell suspension reservoir and/or an excipient reservoir.

4. The bioreactor system of claim 1, wherein said first support element (4a) or both said first and second support elements is/are connected to a respective coupling element (8) which allows the coupling of a sensor device, a measuring device and/or a force-generating device to the respective one of the first support element (4a) and the second support element (4b).

5. The bioreactor system of claim 1, wherein said system further comprises one or more of the following:
   a sterilization unit;
   an electrical pacing device;
   a source for high-energy blue light for optogenetic applications or optical pacing; and/or
   a microscopic device for imaging purposes.

6. The bioreactor system of claim 1, wherein the at least one side wall (3) is made of a flexible or semi-flexible material-such as silicone.

7. The bioreactor system of claim 6, wherein said flexible or semi-flexible material is silicone.

8. The bioreactor system of claim 1, wherein at least said first support element (4*a*) or both said first and second support elements of the reaction chamber comprises a bio-compatible metallic material.

9. The bioreactor system of claim 8, wherein said bio-compatible metallic material comprises titanium or a titanium alloy.

10. The bioreactor system of claim 1, wherein at least said first support element (4*a*) or both said first and second support elements of the reaction chamber is able to perform a horizontal movement.

11. The bioreactor system of claim 1, wherein the bottom plate (12) is made of or coated with a compound that inhibits the adhesion of cells.

12. The bioreactor system of claim 1, wherein said engineered tissue construct is a human tissue construct for tissue replacement therapy, drug development, drug screening, toxicity testing, cosmetic studies, safety testing, developmental studies, disease modeling, or food purposes.

13. A method for preparing an engineered tissue construct, said method comprising:

providing a bioreactor system of claim 1, introducing cells and matrix components into the cavity of the cultivation chamber (1) such that said first support element (4*a*) or both said first and second support elements is/are completely submerged in the fluid containing said cells and matrix components;

incubating the cells and matrix components in the cultivation chamber (1) under conditions that allow the formation of a tissue construct in contact with said first support element (4*a*) or both said first and second support elements of the cultivation chamber.

14. The method of claim 13, wherein said incubating comprises the perfusion of the cultivation chamber (1) with culturing medium.

15. The method of claim 13, wherein said engineered tissue construct is a tissue construct for tissue replacement therapy, drug development, drug screening, toxicity testing, cosmetic studies, safety testing, developmental studies, disease modeling, or food purposes.

* * * * *